US00PP26947P2

(12) United States Plant Patent
Hansen

(10) Patent No.: US PP26,947 P2
(45) Date of Patent: Jul. 12, 2016

(54) ×*HEUCHERELLA* PLANT NAMED 'PINK FIZZ'

(50) Latin Name: ×*Heucherella (Heuchera×Tiarella)*
Varietal Denomination: Pink Fizz

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 87 days.

(21) Appl. No.: 14/121,451

(22) Filed: Sep. 8, 2014

(51) Int. Cl.
*A01H 5/12* (2006.01)

(52) U.S. Cl.
USPC ..... Plt./441

(58) Field of Classification Search
USPC ..... Plt./441
See application file for complete search history.

(56) References Cited

PUBLICATIONS

Perennial Resource. *Heucherella* 'Pink Fizz' PPAF, retrieved on Jan. 28, 2016, retrieved from the Internet at <http://www.perennialresource.com/encyclopedia/view/?plant=2447> 3 pp.*

Mamajack's Jun. 17, 2014 retrieved on Jan. 28, 2016, retrieved from the Internet at <http://cubits.org/notfortheserious/thread/view/79224/> 8 pp.*

* cited by examiner

*Primary Examiner* — June Hwu

(57) ABSTRACT

The new hybrid ×*Heucherella* plant named 'Pink Fizz' with moderately palmately lobed foliage mint-green with a chocolate wine underlay following the main veins. ×*Heucherella* 'Pink Fizz' produces numerous tightly arranged panicles just over the foliage, with sterile pink flowers from late spring through summer and exhibits good heat and humidity tolerance.

1 Drawing Sheet

Botanical denomination: ×*Heucherella* (*Heuchera*× *Tiarella*).

Cultivar designation: 'Pink Fizz'.

BACKGROUND OF THE INVENTION

The present invention relates to a new and distinct intergeneric hybrid between Coral Bells and Foam Flower, both in the Saxifragaceae family and given the cultivar name of 'Pink Fizz' with the combined generic epithet ×*Heucherella*. ×*Heucherella* 'Pink Fizz' resulted from an intentional cross between *Heuchera* 'Milan' U.S. Plant Pat. No. 21,682 as the female or seed parent and a proprietary unreleased seedling *Tiarella* K10-20 (not patented) as the male or pollen parent. The new plant was originally given the breeder code of H11-88-05 and was hybridized by Hans A. Hansen at a nursery in Zeeland, Mich., USA on Jun. 27, 2011 and harvested on Aug. 8, 2011. The new plant was selected from among many other crosses and *Heucherella* seedlings growing at the perennial nursery in Zeeland, Mich. which met the rigorous criteria of excellent foliage, flower and habit established as breeding goals. ×*Heucherella* 'Pink Fizz' has been asexually propagated by division of the rhizome at a nursery in Zeeland, Mich. and also by careful tissue culture propagation. The resultant asexually propagated plants have remained stable and exhibit the same characteristics as the original plant.

BRIEF SUMMARY OF THE INVENTION

×*Heucherella* 'Pink Fizz' differs from its parents as well as all other ×*Heucherella* known to the applicant. The most similar cultivars include: ×*Heucherella* 'Gunsmoke' U.S. Plant Pat. No. 22,395, ×*Heucherella* 'Tapestry' U.S. Plant Pat. No. 21,150 and ×*Heucherella* 'Dayglow Pink' U.S. Plant Pat. No. 12,164.

Compared to 'Gunsmoke', the new plant has more mint-green foliage earlier in the season, has more pinkish flowers on shorter, more compact panicles. The leaf blades of 'Pink Fizz' are also less deeply dissected than 'Gunsmoke'. The foliage color of 'Gunsmoke' is much darker green than the mint green of ×*Heucherella* 'Pink Fizz'.

×*Heucherella* 'Tapestry' has foliage with more chartreuse base, with more pronounced color of dark burgundy in the center palm, and the blades are more dissected. The flowers on 'Tapestry' are more separated and on longer panicles.

×*Heucherella* 'Dayglow Pink' has panicles of similar height with simlarly dark pink flowers, but the foliage is nearly solid chartreuse and not the mint-green with the inner palm of chocolate wine coloring.

Compared to the female parent, *Heuchera* 'Milan' with mahogany foliage with silver overlay, the new plant has more deeply dissected foliage with more mint-green coloration in the early in the season and burgundy or chocolate wine coloring in the center of the lobes, the flowers are lighter pink and panicles much shorter. Compared to the proprietary pollen parent, K-10-20, the new plant has more mint-green coloring in the foliage and less dissected leaf blades. The flower color of the male parent is white, whereas the overall flower color of 'Pink Fizz' is pink.

Further comparisons from these and other ×*Heucherella* cultivars with their corresponding U.S. Plant Patent numbers are shown in the table below:

TABLE 1

| CULTIVAR | DISSECTION | HABIT | LEAF COLOR |
|---|---|---|---|
| 'Alabama Sunrise' U.S. Plant Pat. No. 19,611 | moderate | mounding | yellow to lime |
| 'Brass Lantern' U.S. Plant Pat. No. 22,396 | moderate | mounding | brassy |
| 'Burnished Bronze' U.S. Plant Pat. No. 12,159 | deeply | mounding | brown purple |
| 'Chocolate Lace' U.S. Plant Pat. No. 13,701 | deeply | mounding | bronze |
| 'Dayglow Pink' U.S. Plant Pat. No. 12,164 | moderate | mounding | green |
| 'Golden Zebra' U.S. Plant Pat. No. 22,104 | deeply | mounding | yellow |
| 'Gunsmoke' U.S. Plant Pat. No. 22,395 | deeply | mounding | purple with silver |
| 'Heart of Darkness' U.S. Plant Pat. No. 14,489 | shallow | mounding | green |
| 'Kimono' U.S. Plant Pat. No. 12,154 | deeply | mounding | green |
| 'Leapfrog' (co-pending) | shallow | mounding | yellow to lime |
| 'Pink Fizz' | moderate | mounding | mint green |
| 'Quicksilver' U.S. Plant Pat. No. 11,081 | shallow | mounding | bronze with silver |
| 'Redstone Falls' U.S. Plant Pat. No. 22,394 | moderate | trailing | reddish |
| 'Solar Eclipse' U.S. Plant Pat. No. 23,647 | shallow | mounding | yellow to lime |
| 'Solar Power' U.S. Plant Pat. No. 22,427 | moderate | mounding | yellow to lime |
| 'Sunrise Falls' U.S. Plant Pat. No. 23,666 | deeply | trailing | yellow to lime |
| 'Sweet Tea' U.S. Plant Pat. No. 21,296 | moderate | mounding | rose orange |
| 'Tapestry' U.S. Plant Pat. No. 21,150 | deeply | mounding | green |
| 'Yellowstone Falls' U.S. Plant Pat. No. 22,313 | shallow | trailing | yellow to lime |

| CULTIVAR | MARGIN WIDTH | FLOWER COLOR |
|---|---|---|
| 'Alabama Sunrise' U.S. Plant Pat. No. 19,611 | wide | white |
| 'Brass Lantern' U.S. Plant Pat. No. 22,396 | wide | white |
| 'Burnished Bronze' U.S. Plant Pat. No. 12,159 | none | pink |
| 'Chocolate Lace' U.S. Plant Pat. No. 13,701 | none | white |
| 'Dayglow Pink' U.S. Plant Pat. No. 12,164 | moderate | pink |
| 'Golden Zebra' U.S. Plant Pat. No. 22,104 | wide | white |
| 'Gunsmoke' U.S. Plant Pat. No. 22,395 | none | white |
| 'Heart of Darkness' U.S. Plant Pat. No. 14,489 | wide | white |
| 'Kimono' U.S. Plant Pat. No. 12,154 | wide | cream |
| 'Leapfrog' (co-pending) | moderate | white |
| 'Pink Fizz' | wide | pink |
| 'Quicksilver' U.S. Plant Pat. No. 11,081 | none | white |
| 'Redstone Falls' U.S. Plant Pat. No. 22,394 | wide | white |
| 'Solar Eclipse' U.S. Plant Pat. No. 23,647 | narrow | white |
| 'Solar Power' U.S. Plant Pat. No. 22,427 | wide | white |
| 'Sunrise Falls' U.S. Plant Pat. No. 23,666 | moderate | white |
| 'Sweet Tea' U.S. Plant Pat. No. 21,296 | narrow | white |
| 'Tapestry' U.S. Plant Pat. No. 21,150 | wide | pink |
| 'Yellowstone Falls' U.S. Plant Pat. No. 22,313 | moderate | white |

The margin width being used in the table above as the portion of the leaf blade between the leaf edge and the generally darker portion surrounding the veins; where described as "none" there is no darker burgundy surrounding the veins. Leaf color as used in the table above is the outer portion of the leaf and not the venation or darker portion sometimes surrounding or near the vein.

The new plant differs from all *Heuchera*, ×*Heucherella* and *Tiarella* known to the inventor in the following combined traits:

1. The foliage color of ×*Heucherella* 'Pink Fizz' during most of the growing season is mint-green with a chocolate wine underlay following the main veins.
2. The leaf blade shape is moderately lobed with the middle lobe predominant.
3. The pink flowers are tightly arranged on panicles just over the foliage with repeat flowering over an extended period from late spring through summer.
4. Habit is mounded with multiple tightly clustered shoots emerging at the base all season.
5. The plant is robust, seedless, compact and is more heat and sun tolerant than typical ×*Heucherella*.

BRIEF DESCRIPTION OF THE DRAWING

The photographs of the new plant demonstrate the overall appearance of the plant including the unique traits. The plant in the photograph is of a two-year old plant grown in a double-poly coated greenhouse without further shading, with supplemental fertilizer and water as needed at a wholesale perennial nursery in Zeeland, Mich., USA. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
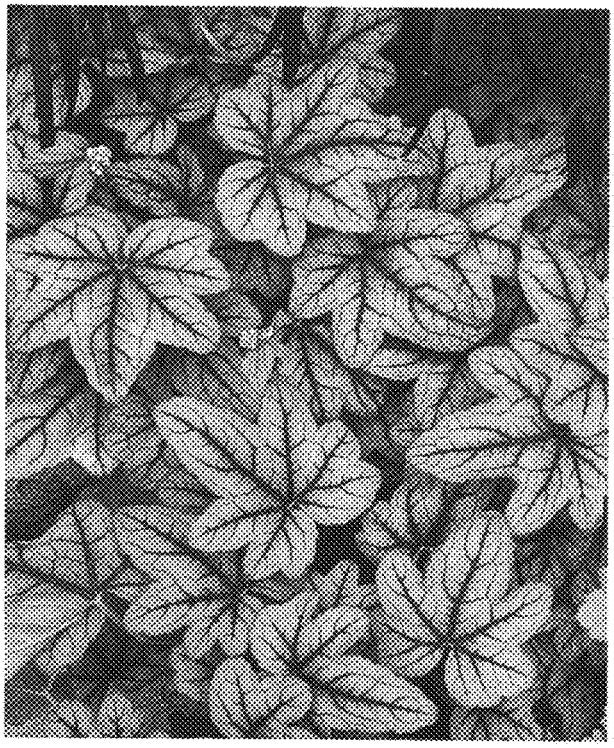
FIG. 1 shows a close-up of the foliage and flower buds.
Figure 2:
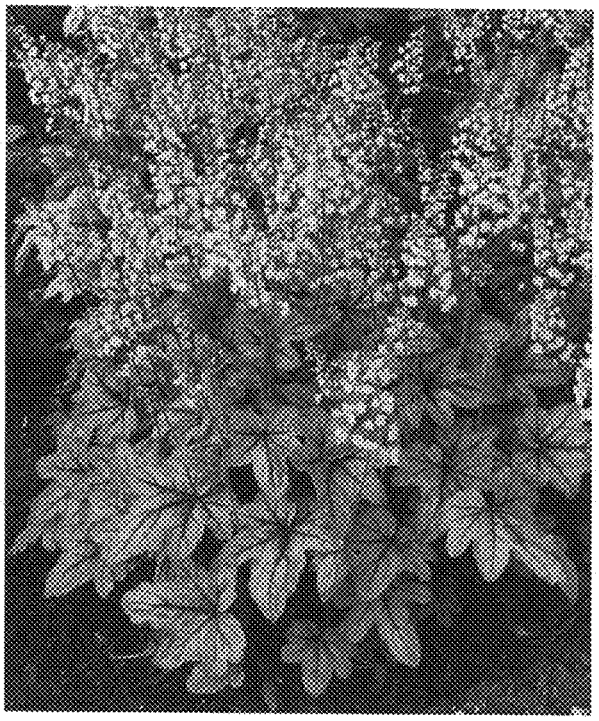
FIG. 2 shows the habit of the plant in mid-season coloration in flower.

The following description is based on two-year old plants growing in double poly greenhouse with supplemental water and fertilizer at a wholesale perennial nursery in Zeeland, Mich., USA as well as three-year old outdoor trial garden grown plants for seasonal foliage coloration comparisons. The new plant has not been grown under all possible environments and may phenotypically appear different under different conditions such as light, temperatures, fertilizer, and water, without any difference in genotype. The color descriptions are from the 2001 edition of The Royal Horticultural Society Colour Chart except where common dictionary terms are used.

Parentage: *Heuchera* 'Milan' U.S. Plant Pat. No. 21,682 the female (seed parent); *Tiarella* K10-20 (not patented) — male (pollen).

Plant habit: Hardy herbaceous perennial of tightly compact rhizomes with basal rosette of mounded foliage; foliage about 15 cm tall and 50 cm in diameter.

Roots: Fibrous, finely branched; when actively growing near white in color depending on soil type.

Growth rate: Rapid, rooting from cutting in 2 weeks and finishing in three-liter container in about 3 months; beginning to flower in 6 to 8 weeks following a 9 week vernalization.

Foliage: Leaf blade — sparsely hirsutulous above and below; palmately lobed, lobes dissected to less than one third of the way to mid-point; matte surface above and below; rounded lobe apices and cordate base; blade to about 11.0 cm long and 10.0 cm wide, average about 8.0 cm long and 9.0 cm wide; with a dark pigment running on the central portion of the lobes expanding in width and density from undertone to solid pattern as foliage matures though season; center lobe to about 4.5 cm long, average about 3.2 cm long and about 50% larger than the length of the next largest side lobes; cauline leaves at first or second nodes directly below lowest flowers, decreasing in size distally; foliage margin indentation is medium.

*Foliage color*.—Leaf color is seasonally variable; spring young emerging leaves adaxial surface nearest RHS N144C with a center inner palm pigmenting of nearest RHS 187B; abaxial spring emerging leaves nearest RHS 144B with inner palm pigmentation of nearest RHS 187C; at first showing of flower buds and until summer heat adaxial blades within 2 mm either side of veins nearest RHS N187A and radiating away from veins between RHS N187B and RHS N187C to a maximum width of about 8.5 mm, and outer (marginal) adaxial portion between RHS 138B and RHS 138C; at first showing of flower buds and until summer heat abaxial blades near veins between RHS 138B and RHS 138C with undertones of nearest RHS N187B and outer blade portion between RHS 138B and RHS 138C; mid-season adaxial mid-portion near veins between RHS N186B and RHS N187A and outer portion between RHS 148B, RHS 148C and RHS 191B; mid-season abaxial mid-portion near veins nearest RHS 148D with broad section having undertones of nearest RHS N187B and outer portion between RHS 148D and RHS 146D; overwintered leaves in spring adaxial portion near veins nearest RHS N187A and outer portion between RHS N138C and RHS 138B with tinting of RHS 187B; overwintered leaves abaxial variable between RHS 185B and RHS 186A with green undertones of RHS 138A.

*Leaf margin*.—Crenate to serrate, hirsutulous.

*Leaf apex*.—Obtuse to cuspidate; hirsutulous.

*Leaf base*.—Cordate with frequently overlapping lobes.

*Leaf surface*.—Sparsely hirsutulous both above and below.

*Leaf quantity*.—Dens; about seven per division and 250 per plant.

*Veins*.—Palmate, hirsutulous below and sparsely hirsutulous above.

*Vein color*.—Adaxial early expanding foliage nearest RHS 145C and abaxial between RHS 145C and RHS 145D; at time of beginning flowering adaxial main veins nearest RHS 145B and outer smaller veins between RHS 144A and RHS 144B; at time of beginning flowering abaxial main veins between RHS 145B and RHS 145C; mid-summer adaxial veins between RHS N144D and RHS 145C and abaxial main veins nearest RHS 145C with secondary veins between RHS 147A and RHS 146A; overwintered adaxial veins between RHS 194A and RHS 160D and overwintered abaxial main veins nearest RHS 147D with light tinting of RHS 181B and abaxial secondary veins nearest RHS 139A.

Petiole: Cylindrical, hirsutulous, average about 12.0 cm long and 2.5 mm diameter at base; wiry but flexible.

*Petiole color*.—On emerging foliage between RHS 144C and RHS N144D; mid-flowering season and later nearest RHS 144C; on overwintered foliage nearest RHS 146D with tinting of nearest RHS 185A.

Inflorescence: In compacted panicle or branched raceme, about 60 racemes per plant; about 60 flowers per raceme; first raceme flowering beginning in late spring with repeat racemes flowering until fall; individual racemes remaining in flower for about two and a half weeks; individual flowers remaining open about three to four days; flower attitude mostly outwards.

Fragrance: None detected.

Peduncle: Round in cross section; glandular, hirsutulous; about 38 cm tall and 3.0 mm diameter at base; with cauline leaves at one to two nodes directly below lowest flowers and dehiscent bracts at lowest one or two nodes; flowering portion about 13.5 cm long and 5.5 cm across.

*Peduncle attitude*.—Upright; erect.

*Peduncle branches*.—In lower two thirds of peduncle with average of 3.5 flowers per branch; branches about 2.5 cm long and about 1.5 mm diameter at base.

*Peduncle color*.—Between RHS 145C and RHS145D in lowest portion, nearest RHS 144B in middle portion and nearest RHS 176B with green undertone of nearest RHS 144A in upper portion.

Cauline leaves: Average 3.5 cm across and 4.0 cm long with petioles about 2.8 cm long and 1.5 mm diameter a base, color of cauline leaves and petioles same as other foliage with less pronounced or no burgundy centers.

Dehiscent lower bracts: Lanceolate, sessile, acute apex, truncate base, entire margin, about 1.2 mm long and 5.0 mm across at peduncle; color before dehiscing nearest RHS N155B along center vein and nearest RHS 155C and translucent along margin.

Pedicel: Round in cross section; glandular, hirsutulous; about 2.0 mm long and 0.8 mm in diameter.

*Pedicel color*.—Nearest RHS 183C with green undertones of nearest RHS 137C becoming more greyed purple with more light.

Bracts at peduncle branches: Mostly lobed, lanceolate, acute apex and sessile base; lower bracts about 6.0 mm long and 2.0 mm wide at widest point in center decreasing in size distally.

*Bract color*.—Proximal bracts abaxial and adaxial between RHS 138B and RHS 138A with no noticeable center burgundy tinting nearest RHS 187B on lobe apexes; distal bracts on both abaxial and adaxial surfaces nearest RHS 185A with green undertones along the center vein of nearest RHS 138A.

Buds one day prior to opening: Slightly oblong, about 3.5 mm long and 3.0 mm diameter.

*Bud color*.—Between RHS 185C and RHS 186A.

Flower: Perfect, campanulate; about 7.0 mm deep and 9.0 mm in diameter at face; individual flowers lasting about three to four days on plant or as cut raceme.

Calyx: Five sepals; glandular outside, glabrous inside; apex acute, fused at base into bypanthium; margin entire; sepals about 6.5 mm long extending about 3.5 mm beyond point of fusion and about 2.5 mm wide at point of fusion, calyx about 5.0 mm across and 5.5 mm deep.

*Calyx color*.—Adaxial between RHS 186C and RHS 64C; abaxial nearest RHS 64D and darkening to between RHS 64D and RHS 64C at apex.

Petals: Five; adnate to calyx; spatulate, narrowly acute apex, attenuate base; margin entire; puberulent outside and glabrous inside; about 5.0 mm long and 1.5 mm wide.

*Petal color*.—Abaxial lighter than RHS N155D; adaxial near white, lighter than RHS N155D.

Androecium:

*Filaments*.—Up to ten, thin, about 3.5 mm long and less than 0.5 mm in diameter; color white, lighter than RHS N155D.

*Anthers*.—Basifixed; oblong to nearly 0.5 mm long and less than half as wide; color between RHS 20A and RHS 163B.

*Pollen*.—Not observed under present conditions.

Gynoecium:

*Pistil*.—One central two-beaked pistil, about 5.0 mm long and 0.2 mm at apex flaring to 2.0 mm at base; color nearest RHS 155D.

*Stigma*.—Minute, about 0.2 mm diameter; color nearest RHS 155D.

*Ovary*.—Two carpels; ovoid, apex tapering to meet style; rounded base and sides; about 2.0 mm across at base and 2.5 mm tall; color nearest RHS 155D.

Fruit and seed: Not observed.

Disease and pest tolerance: ×*Heucherella* 'Pink Fizz' grows best with ample moisture and good drainage in part shade or protection from sun in the hottest part of the day. Cold hardy from USDA zones 4 to 9. ×*Heucherella* 'Pink Fizz' is able to tolerate heat and humidity better than many ×*Heucherella*. Other pest and disease resistance and tolerance outside of that normal for ×*Heucherella* is not known.

I claim:

1. The new and distinct ornamental plant named ×*Heucherella* 'Pink Fizz' as herein described and illustrated with seasonally variably colored foliage and numerous pink flowers on short compact panicles over a long period of time, with improved heat tolerance suitable for landscaping or as an ornamental container plant.

* * * * *